United States Patent
Williams

(10) Patent No.: US 10,960,060 B1
(45) Date of Patent: Mar. 30, 2021

(54) TREATMENT OF CARDIAC ARRHYTHMIA USING BOTULINUM TOXIN

(71) Applicant: PENLAND FOUNDATION, Beaumont, TX (US)

(72) Inventor: Roland M. Williams, Beaumont, TX (US)

(73) Assignee: PENLAND FOUNDATION, Beaumont, TX (US)

( * ) Notice: Subject to any disclaimer, the term of this patent is extended or adjusted under 35 U.S.C. 154(b) by 0 days.

(21) Appl. No.: 16/875,945

(22) Filed: May 15, 2020

Related U.S. Application Data

(63) Continuation-in-part of application No. 16/657,933, filed on Oct. 18, 2019, now Pat. No. 10,722,552, and a continuation-in-part of application No. 16/657,950, filed on Oct. 18, 2019, now abandoned.

(51) Int. Cl.
    *A61K 38/48* (2006.01)
    *A61P 9/06* (2006.01)
    *A61K 9/00* (2006.01)

(52) U.S. Cl.
    CPC ........ *A61K 38/4893* (2013.01); *A61K 9/0019* (2013.01); *A61P 9/06* (2018.01); *C12Y 304/24069* (2013.01)

(58) Field of Classification Search
    None
    See application file for complete search history.

(56) References Cited

U.S. PATENT DOCUMENTS

| | | | |
|---|---|---|---|
| 5,766,605 A | 6/1998 | Sanders et al. | |
| 6,063,768 A | 5/2000 | First | |
| 6,139,845 A | 10/2000 | Donovan | |
| 6,632,440 B1 | 10/2003 | Quinn et al. | |
| 6,977,080 B1 | 12/2005 | Donovan | |
| 7,655,244 B2 | 2/2010 | Blumenfeld | |
| 8,734,810 B2 | 5/2014 | Blumenfeld | |
| 9,254,314 B2 | 2/2016 | Finzi et al. | |
| 9,707,207 B2 | 7/2017 | Finegold | |
| 10,011,823 B2 | 7/2018 | Barbieri et al. | |
| 10,258,673 B2 | 4/2019 | Pokushalov et al. | |
| 10,722,552 B1 | 7/2020 | Williams | |
| 2004/0062776 A1 | 4/2004 | Voet | |
| 2004/0220544 A1 | 11/2004 | Heruth et al. | |
| 2005/0147626 A1 | 7/2005 | Blumenfeld | |
| 2005/0191320 A1 | 9/2005 | Turkel et al. | |
| 2007/0259002 A1 | 11/2007 | Batchelor | |
| 2009/0142430 A1 | 6/2009 | Sanders et al. | |
| 2009/0232850 A1 | 9/2009 | Manack et al. | |
| 2010/0303788 A1 | 12/2010 | Francis et al. | |
| 2011/0200639 A1 | 8/2011 | Blumenfeld | |
| 2012/0093827 A1 | 4/2012 | Van Schaack et al. | |
| 2012/0195878 A1* | 8/2012 | Haag-Molkenteller | A61P 25/06 424/94.67 |
| 2012/0244188 A1 | 8/2012 | Blumenfeld et al. | |
| 2012/0251519 A1 | 10/2012 | Blumenfeld et al. | |
| 2013/0251830 A1 | 9/2013 | Manack et al. | |
| 2015/0086533 A1 | 3/2015 | Borodic | |
| 2017/0173123 A1 | 6/2017 | Blumenfeld | |
| 2017/0333537 A9* | 11/2017 | Borodic | A61K 9/0019 |
| 2018/0071361 A1* | 3/2018 | Abiad | A61P 9/06 |
| 2019/0038646 A1* | 2/2019 | Bright | A61P 29/00 |
| 2019/0300583 A1 | 10/2019 | Jarpe | |

FOREIGN PATENT DOCUMENTS

| | | | |
|---|---|---|---|
| EP | 2072039 A1 | 6/2009 | |
| JP | 2012107051 A | 6/2012 | |
| KR | 20100032982 A | 3/2010 | |
| KR | 20150126979 A | 11/2015 | |
| WO | WO 95/28171 | 10/1995 | |
| WO | WO 00/10598 | 3/2000 | |
| WO | WO 01/10458 * | 2/2001 | ............. A61K 38/16 |
| WO | WO 01/104058 A | 2/2001 | |
| WO | WO2010013495 A1 | 2/2010 | |
| WO | WO2011084507 A | 7/2011 | |
| WO | WO 2014/184746 * | 11/2014 | ............... A61K 9/00 |

OTHER PUBLICATIONS

The Harvard Medical School website; downloaded Jul. 18, 2020 from: https://www.health.harvard.edu/a_to_z/cardiac-arrhythmias-a-to-z; 5 pages total (Year: 2020).*
Machine translation of the foreign patent document, KR20100032982, 7 pages total (Year: 2010).*
Oomens and Forouzanfar, Drugs Aging (2015) 32:717-726 (Year: 2015).*
Frank CT Smith, Vascular Surgery—II, 2013; 31: 251-255; doi: https://doi.org/10.1016/j.mpsur.2013.03.005 (Year: 2015).*
Machine translation of WO2010/013495 document submitted on the IDS filed Feb. 10, 2021; 25 pages (Year: 2021).*
Pugh KR et al, Abstract—"Glutamate and choline levels predict individual differences in reading ability in emergent readers", J.Neurosci. Mar. 12, 2014;34(11):4082-9. doi: 10.1523/JNEUROSCI. 3907-13.2014 https://www.ncbi.nlm.nih.gov/pubmed/24623786 (Dec. 13, 2019).
Ryan J. Diel, MD et al, "Photophobia and sensations of dryness in migraine patients occur independent of baseline tear volume and improve following botulinum toxin A injections", HHS Public Access, Br J Ophthalmol. Author manuscript; available in PMC Aug. 1, 2019, pp. 1-15.
Donald C. Rojas, "The role of glutamate and its receptors in autism and the use of glutamate receptor antagonists in treatment", J Neural Transm. Aug. 2014 ; 121(8): 891-905, pp. 1-24.

(Continued)

*Primary Examiner* — Christina M Borgeest
(74) *Attorney, Agent, or Firm* — Winston & Strawn LLP

(57) ABSTRACT

A method for treating arrhythmia in a patient in need thereof comprises administering botulinum toxin to the patient. Botulinum toxin may be administered by subcutaneous or intradermal injection. The subcutaneous or intradermal injection may be administered to and/or around the vicinity of a trigeminal nerve, a cervical nerve, a thoracic nerve, a lumbar nerve, and/or a sacral nerve of the patient.

18 Claims, No Drawings

(56) References Cited

OTHER PUBLICATIONS

Juan M. Espinosa-Sanchez et al, "New insights into pathophysiology of vestibular migraine", Frontiers in Neurology, Feb. 2015 | vol. 6 | Article 12, pp. 1-6.
Colleen Doherty, MD, "The Link Between Migraines and Tinnitus, Buzzing or ringing in your ears could be related to your episodes", VeryWell Health, Aug. 6, 2019, pp. 1-13 https://www.verywellhealth.com/link-between-migraines-and-tinnitus-4077631.
K,J. Powell et aL, "The Role of CGRP in the Development of Morphine Tolerance and Physical Dependence", 4th International Meeting on Calcitonin Gene-Related Peptide (CGRP), The ScientificWorld (2001) 1 (S1), 21. 2 pages.
Vacca et al., "Botulinum Toxin A Increases Analgesic Effects of Morphine, Counters Development of Morphine Tolerance and Modulates Glia Activation and μ Opioid Receptor Expression in Neuropathic Mice", Brain, Behavior, and Immunity 32 (2013), pp. 40-50 (Year: 2013).
Mayo clinic article, "Autism Spectrum Disorder", Symptoms and Causes, 5 pages (Year: 2019) downloaded on Dec. 23, 2019 from: https://www.mayoclinic.org/diseases-conditions/autism-spectrum-disorder/ symptoms-causes/syc-20352928?p=1.
The Machine Translation of WO2010013495, English Abstract,"Pharmaceutical Composition Containing Highly Purified Botulinum Neurotoxin Therapeutic Agent as Active Ingredient, and Use Thereof", Akaike et al.; Feb. 4, 2010 (Year: 2010).
Nair et al., "Impaired Thalamocortical Connectivity in Autism Spectrum Disorder: A Study of Functional and Anatomical Connectivity", Brain, Journal of Neurology, 2013; 136: 1942-1955 (Year: 2013).
Panju et al., "Atypical Sympathetic Arousal in Children With Autism Spectrum Disorder and Its Association With Anxiety Symptomatology", Molecular Autism (2015) 6:64, pp. 1-10 (Year: 2015).
Saunte et al., "Improverment in Reading Symptoms Following Botulinwn Toxin A Injection for Convergence Insufficiency Type Intermittent Exotropia", Acta Ophthalmologica (1755375X). Aug. 2015, vol. 93 Issue 5, pp. 1-3 (Year: 2015).
The WebMD website, "Treatments for Dyslexia", The International Dyslexia Association National Center for Learning Disabilities. National Center for Neurological Disorders and Stroke, https://www.webmd.com/children/dyslexia-treatments; accessed Jun. 22, 2020 , 1 page, (Year: 2020).
Hulme et al., "Reading Disorders and Dyslexia", Current Opinion Pediatrics2016, 28: pp. 731-735 (Year: 2016) www.co-pediatrics.com.
Mazzone et al., "Vaginal Afferent Innervation of the Airways in Health and Disease", Physiol Rev 96: 975-1024, 2016, pp. 975-1024, (Year: 2016).
Schematic of innervation of organs, available from https://ars.els-cdn.com/content/image/3-s2.0-B9780323378048000055-f005-001-9780323378048.jpg, downloaded Jun. 22, 2020 and reproduced within the Office action (Year: 2020).
The Harvard Medical School , "Cardiac Arrhythmias", Harvard Health Publishing, Published Feb. 2019. website; downloaded Jul. 18, 2020 from: https://www.health.harvard.edu/a_to_z/ cardiac-arrhythmias-a-to-z; 5 pages total (Year: 2020).
Machine English Translation of the foreign patent document, KR20100032982, 7 pages total (Year: 2010).
Mitchell and Borasio et al., "Amyotrophic Lateral Sclerosis", Seminar, Lancet 2007; vol. 369: 2 pp. 2031-2041 (Year: 2007).
S. Kumar, "The Emerging Role of Botulinum Toxin in the Treatment of OroFacial Disorders: Literature Update", Asian Journal Pharm Clin Res, vol. 10, Issue 9, 2017, pp. 21-29 (Year: 2017).
Lewitt and Trosch, et al., "Idiosyncratic Adverse Reactions to Intramuscular Botulinum Toxin Type A Injection", Movement Disorders, 1997; 12: pp. 1064-1067 (Year: 1997).
Squires et al., "The Use of Botulinum Toxin Injections to Manage Drooling in Amyotrophic Lateral Sclerosis/Motor Neurone Disease: A Systematic Review", Dysphagia (2014) 29: pp. 500-508 (Year: 2014).
The website downloaded on Jul. 2, 2020 from Juvenile Amyotrophic Lateral Sclerosis,Genetic and Rare Diseases Information Center (GARD)—an NCATS Program, https://rarediseases.info.nih.gov/diseases/11901/juvenile-amyotrophic-lateral-sclerosis; Jul. 2, 2020, 8 pages total (Year: 2020).
Mortazavi et al., "Xerostomia Due to Systemic Disease: A Review of 20 Conditions and Mechanisms", Ann Med Health Sci Res. Jul.-Aug. 2014; 4(4): 503-510. doi: 10.4103/2141-9248.139284: 10.4103/2141-9248.139284,15 pages (Year: 2014).
The website downloaded Jul. 21, 2020 from Children's Hospital of Pittsburgh , "Cirrhosis in Children: Symptoms and Treatment", UPMC, 4 pages total . Jul. 21, 2020 (Year: 2020) (https://www.chp.edu/our-services/transplant/liver/ education/liver-disease-states/cirrhosis.
Fernandez-Rodriguez et al., "Plasma Levels of Substance P in Liver Cirrhosis: Relationship to the Activation of Vasopressor Systems and Urinary Sodium Excretion", Hepatology, Jan. 1995; 21: pp. 35-40,(Year: 1995).
Glatte et al., "Architecture of the Cutaneous Autonomic Nervous System", Frontiers in Neurology, vol. 10, Article 970, 2019, pp. 1-11, 10: doi: 10.3389/fneur.2019.00970 (Year: 2019) Sep.
Web Article: Neuroscience, what-when-how, In Depth Tutorials and Information, Gross Anatomy of the Brain, Dec. 7, 2020, 2 pages, The autonomic system schematic downloaded Nov. 23, 2020 from http://what-when-how.com/neuroscience/ the-autonomic-nervous-system-integrative-systems-part-1/; the image is reproduced in the Office action (Year: 2020).
WebMD, ADHD and Dyslexia: How to Tell Them Apart, Dyslexia and ADHD Similarities and Differences, Nov. 30, 2020, 3 pages, The article downloaded Nov. 30, 2020 from https://www.webmd.com/add-adhd/adhd-dyslexia-tell-apart?print=true; 3 pages total (Year: 2020) WebMD.
Chien et al., "Sympathetic Fiber Sprouting in Chronically Compressed Dorsal Root Ganglia Without Peripheral Axotomy", NIH Public Access, Author Manuscript of J. Neuropathic Pain Symptom Palliation. 2005; 1 (1 ): pp. 19-23 (Year: 2005).
Scott and Fryer, "Role of Parasympathetic Nerves and Muscarinic Receptors in Allergy and Asthma", NIH Public Access, Author Manuscript of Chem Immunol Allergy. 2012; 98: pp. 48-69 (Year: 2012).
Web Article, The image downloaded Dec. 4, 2020 from https://nursing-skills.blogspot.com/2014/01/angle-of-injection.html; image reproduced in Office action (Year: 2020.
Dobrek and Thor, "Glutamate NMDA Receptors in Pathophysiology and Pharmacotherapy of Selected Nervous System Dseases", Postepy Hig Med Dosw (online), 2011; 65: pp. 338-346 , 1 Year: 2011).
Erle CH Lim, "Botulinum toxin, Quo Vadis?", Elsevier Ltd., Medical Hypotheses (2007) 69, pp. 718-723 (Year: 2007) http://inti.elsevierhealth.com/journals/ mehy.
International Search Report and Written Opinion, PCT/US2020/056206, dated Feb. 1, 2021.

* cited by examiner

TREATMENT OF CARDIAC ARRHYTHMIA USING BOTULINUM TOXIN

This application is a continuation-in-part of U.S. patent application Ser. No. 16/657,933 and U.S. patent application Ser. No. 16/657,950, filed Oct. 18, 2019, respectively. The entirety of each prior application is expressly incorporated herein by reference thereto.

FIELD OF THE INVENTION

The present invention generally relates to methods for diagnosing and treating (including alleviating and/or preventing) some of the 30% of cardiac arrhythmias of unknown causes and possibly arrhythmias of known causes whose treatments are not totally successful and may be complicated by neuropathic conditions.

BACKGROUND OF THE INVENTION

Botulinum toxins cleave and destroy a protein called synaptosomal nerve-associated protein 25 ("SNAP25") and/or synaptobrevin (also called vesicle-associated membrane protein ["VAMP" ]). Botulinum toxins A, C, and E cleave SNAP25 at different locations, but the effect is in general the same—the protein is destroyed and cannot function until the cell makes new ones. Botulinum toxins B, D, F, and G cleave VAMP present at the cytoplasmic surface of the synaptic vesicle. The two important locations in the body where the proteins are found are at the terminals of the motor neurons (muscle) and in the cell membrane of astrocytes, glial cells, and satellite cells. These three cell types surround sensory neurons and form part of the blood-brain barrier. In motor nerves, to cause them to fire, vesicles of acetylcholine move from inside the motor neuron across the cell membrane at the synapse between the motor nerve and muscle fiber. Acetylcholine is released into the synapse and activates receptors in the muscle fiber, which contracts the muscle fiber. In sensory nerves, when a nerve is damaged from physical or mental injuries, the three aforementioned structural cells produce large amounts of Substance P, Calcitonin Gene Related Peptide (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules bind to the receptor on the sensory nerves, causing the neuroexcitatory effects. The molecules can also diffuse in the cerebrospinal fluid (CSF) and influence other sensory nerves to become hyperactive, a process called central sensitization.

This mechanism of cleaving the SNAP25 and/or VAMP in muscles and sensory nerves causes the only known clinical effects of botulinum, which paralyzes muscles in the motor system for 3-4 months until the cell grows a new protein. This effect has been used for decades for overactive muscles (such as in cervical dystonia, blepharospasm, tic, Parkinson's, cerebral palsy, etc.), wrinkles in the face, excessive sweating, and overactive bladder.

In the sensory nerves, the mechanism has been used for migraines and depression. The effect of blocking the SNAP25 and/or VAMP in the glial, satellite, and astrocyte cells will work for 5-9 months until these cells grow new proteins. The important part of this mechanism is that the botulinum effect does not destroy cells and does not stop the normal production of or effects of acetylcholine (muscles) or Substance P, CGRP, or glutamate in sensory nerves. These facts give huge advantages over a monoclonal antibody which would eliminate all glutamate, CGRP, and Substance P. Side effects of such elimination would be disastrous. The receptor antagonists also have problems—for example, because the receptor antagonists are not site-specific, they block glutamate, Substance P, and CGRP everywhere. Too little glutamate, Substance P, and/or CGRP is a problem, as well as too much. It is difficult to regulate oral or I.V. doses to obtain the correct level of reduction in areas that are too high in glutamate, Substance P, and/or CGRP without over-reduction in areas with normal levels. Additionally, TENS, which are only a functional portion of the botulinum toxin molecule, are hoped to one day reduce the muscular side effects of the use of botulinum toxin for neuropathic conditions. TENS, however, are known to have not been developed or tested yet.

Small doses of botulinum toxin injected into a specific muscle can cleave SNAP25 and/VAMP to calm the muscle's overreaction or paralyze the muscle temporarily if desired. Or, if injected subcutaneously near unmyelinated sensory nerves, the botulinum toxin can stop the overproduction of the sensory neuroexcitatory compounds without affecting normal glutamate, Substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage, and injection must be done with knowledge and care.

In particular, the mechanism of the sensory effect (stopping overproduction of glutamate, Substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess Substance P, CGRP, and glutamate, which is involved in the neural injury response mechanism without affecting normal glutamate, Substance P, and CGRP production, use, or receptors. An example of a malfunction with the normal nerve mechanism is an infection of a nerve by the shingles virus. The infection by the shingles virus damages the nerve but does not kill it, or there would be no feeling (numbness). This causes a spike in the production of glutamate, Substance P, and CGRP, leading to the well-known shingles pain and hypersensitivity. Over a 2-3 month period, the infection is controlled, the nerve heals, and the overproduction of the neuroexcitatory chemical gets back to normal. However, sometimes for unknown reasons, the overproduction does not get back to normal but remains high and severe chronic pain and hypersensitivity persists. Chronically overstimulated neurons can cause numerous problems depending on where the neurons are located. The neuroexcitatory chemicals can travel up the spinal cord to the brain in the CSF and affect neurons there. This process is called central sensitization. Depending on where glutamate, Substance P, and CGRP are produced and where the molecules travels to, the molecules can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances, and perhaps the death and malformation of the developing neural architecture in children with ASD (autism).

SUMMARY OF THE INVENTION

The claimed invention is related to methods for treating arrhythmia in a patient in need thereof. The method comprises administering botulinum toxin to the patient. Botulinum toxin may be administered by subcutaneous or intradermal injection. The subcutaneous or intradermal injection may be administered to and/or around the vicinity of a trigeminal nerve of the patient. The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, greater occipital nerve, or a combination thereof. The subcutaneous or intradermal injection may be administered to and/or around the vicinity of a cervical nerve of the patient. The selected cervical nerve comprises the c-2 nerve, c-3 nerve, c-4 nerve, c-5 nerve, c-6 nerve, c-7 nerve, c-8 nerve, or a combination thereof. The subcutaneous or intradermal injection may be administered by subcutaneous or intradermal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises the 1-1 nerve, 1-2 nerve, 1-3 nerve, 1-4 nerve, 1-5 nerve, or a combination thereof. The subcutaneous or intradermal injection may be administered to and/or around the vicinity of a sacral nerve of the patient. The selected sacral nerve comprises the s-1 nerve, s-2 nerve, s-3 nerve, s-4 nerve, s-5 nerve, or a combination thereof. In some embodiments, the subcutaneous or intradermal injection may be administered to and/or around the vicinity of a trigeminal nerve, a cervical nerve, a thoracic nerve, a lumbar nerve, a sacral nerve, or a combination thereof of the patient. Preferably, the administering for an adult who weighs about 150 lbs comprises by subcutaneous or intradermal injection 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2, 1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). The dosage of botulinum toxin for an adult, a child or a toddler from about 1 to 5 years old is adjusted for age and weight. The administering for a toddler from about 1 to 5 years old is adjusted for age and weight. In some desired embodiments, the botulinum toxin comprises botulinum toxin type A, botulinum toxin type B botulinum toxin type C, botulinum toxin type D, botulinum toxin type E, botulinum toxin type F, botulinum toxin type G, a fragment thereof, a hybrid thereof, a chimera thereof, or a combination thereof.

DETAILED DESCRIPTION OF THE PREFERRED EMBODIMENTS

Further in relation to this, before explaining at least the preferred embodiments of the invention in greater detail, it is to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth herein means±10% of the numerical value or range recited or claimed.

The term "treating" includes delaying, alleviating, mitigating, or reducing the intensity, progression, or worsening of one or more attendant symptoms of a disorder or condition and/or alleviating, mitigating or impeding one or more causes of a disorder or condition. Treatment under the claimed invention may be a preventative treatment, prophylactic treatment, remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease, its severity, and the age, weight, etc. of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

In accordance with the principles of the present invention, use of botulinum toxin to treat cardiac arrhythmias is provided.

Heart Arrhythmia

A cardiac arrhythmia or an arrhythmia is a variation from the normal heart rate or rhythm that is not physiologically justified. A cardiac arrhythmia is characterized by irregular rhythm of heartbeat which could be either too slow (<60 beats/min) or too fast (>100 beats/min) and can happen at any age.

An arrhythmia can be caused by many different factors, including, but not limited to: organic heart defect, valvular heart disease, coronary artery disease, hypertension, hypertrophic cardiomyopathy, dilated cardiomyopathy, congenital heart disease, atrial septal defect/mitral valve prolapse, cardiac amyloidosis, hemochromatosis, endomyocardial fibrosis, calcification of the mitral annulus, atrial myxoma, pheochromocytoma, and idiopathic dilated right atrium.

Atrial fibrillation in about 30% of the cases occurs without any detectable etiology including, but not limited to, rare cases of Wolff-Parkinson-White Syndrome, hyperthyroidism, chronic obstructive lung disease, and sinus node destruction.

If not properly treated, development of blood clots (emboli) can enter the circulation and cause stroke, heart attack, heart failure, or sudden cardiac failure. Symptoms include lightheadedness, dizziness, and syncope (fainting).

Current Treatment

If organic or structural defects are present, then they may be treatable by drugs 1) anticoagulants to prevent blood clot formation; or 2) adenosine, atropine, beta blockers, calcium channel blockers, potassium channel blockers, or sodium channel blockers to slow a racing heart rate. There are other treatments (e.g., surgical procedures to repair structural defects.) that do not use drugs but they all have some drawbacks. For example, a catheter may cause serious obliteration of nerves; a pacemaker requires a surgery to install or place it in a patient's body and needs to shock the heart to restore a normal rhythm; and an implantable defibrillator pacemaker is not patient-friendly.

While 2-3% of the US population (roughly 7-8 million people) is estimated to have cardiac arrhythmia, the arrhythmias of 30% of these patients (roughly 2.5 million people) are of unknown or unexplained origin.

Normal Neural Control of Heart Rate

The neural control of heart rate is as follows: the vagus nerve (the tenth cranial nerve or CN X) supplies parasympathetic innervation to the heart, which slows the heart rate. On the other hand, the sensory nerves originating in the t-1 to t-3 spinal nerves increase the heart rate. Spinal nerves t-6 to t-8 also affect the heart rate by innervating the adrenal glands. When the adrenal glands are stimulated, they release epinephrine and norepinephrine, which increase heart rate.

According to oxygen and blood demand, the brain controls the heart rate. When more blood and oxygen are needed, the t-1 to t-3 area is stimulated to increase the heart rate. When a sudden burst of blood and oxygen is needed (e.g., during an emergency such as fight or flight reflex), the adrenal glands are stimulated to release epinephrine and norepinephrine. When extra oxygen and blood flow is not needed anymore, the vagus nerve slows the heart rate, and the brain stops stimulating the thoracic nerves involved in raising the heart rate.

Mechanism of Cause of these Arrhythmias

The following treatment of the present application is to address at least a portion of the 2.5 million people who have an unexplained cause of arrhythmias and must sometimes undergo a cardiac obliteration procedure, which obliterates nerves that go to the heart, take surgical risks associated with the placement of a pacemaker, or tolerate side effects associated with medication. The possible cause of some of these arrhythmias could be neuropathic hypersensitivity of the t-1 to t-3 and t-5 to t-8 sensory spinal nerves caused by the overproduction of the neuroexcitatory substances glutamate, Substance P, and CGRP. In these conditions, the blood, CSF, and brain levels of these substances are vastly increased. These substances cause hypersensitivity to the involved sensory nerves and increase neural firing with minimal stimulation. When the increased neural firing happens in the t-1 to t-3 area, the increased neural hypersensitivity causes increased firing from the normal brain stimulation of the nerve, resulting in an increased heart rate. When the increased neural firing happens in the t-5 to t-8 area, the excess stimulation and neural firing result in signals to the adrenal gland, which cause excess release of epinephrine and norepinephrine which also make the heart rate increase. The increased heart rate is detected by the brain, which increases firing of the vagus nerve in response and thus slows the heart back down. The entire process results in the up and down swing in heart rate, which is characteristic of some arrhythmias.

Proposed Treatment

If a physician cannot find one of the pathogenic causes, then a blood test can be done to see if there are elevated levels of glutamate, Substance P, and CGRP. By conducting a blood test, the patient's physical symptoms of other neuropathic symptoms such as migraine and fibromyalgia that have shown to be comorbid with cardiac arrhythmia can be evaluated. If there are positive findings then botulinum toxin can be given to lower the excess glutamate, Substance P, and CGRP and stop the excess firing of the spinal sensory nerves and the seesaw effect of the vagus nerve lowering of heart rate and sensory elevation.

Not wishing to be bound by any theory, one of the causes of unknown arrhythmias can be due to excess levels of glutamate, Substance P, and CGRP in the brain, CSF, or blood wherein the excess levels cause neuropathic hypersensitivity in the t-1 to t-3 and t-5 to t-8 dermatomes. Excess glutamate, Substance P, and CGRP cause nerves in the t-1 to t-3 area which, when firing, increase heart rate to become hypersensitive and fire more than necessary, thus increasing the heart rate more than the brain intends. Overactive sensory nerves in the t-5 to t-8 area overstimulate the adrenal glands, causing excess release of epinephrine and norepinephrine that also cause a spike in the heart rate. The brain, recognizing the existence of an unnecessary increase in the heart rate, stimulates the vagus nerve in response to slow down the heart. These reactions create a cycle of elevated and decreased heart rates. Subcutaneous administration of botulinum toxin can control the excess glutamate, Substance P, and CGRP with the resulting neural hypersensitivity, thereby treating or alleviating the arrhythmia.

Known methods for using botulinum toxin to treat arrhythmia involve treating the local nerve or muscle that is causing the excitement of the nerve or muscle that is establishing arrhythmia. In contrast, the methods according to embodiments of the present invention involve administering botulinum toxin by subcutaneous or intradermal injection at locations where the overproduction of Substance P, CGRP, and glutamate causes hypersensitivity to the involved sensory nerves, increasing the reaction from the normal brain stimulation of the nerve and ultimately resulting in an increased heart rate, which can be effectively inhibited while maintaining regular production of Substance P, CGRP, and glutamate. The methods according to embodiments of the present invention are preferably applied to all or many of these locations. Depending on symptoms or conditions, the botulinum toxin used in embodiments of the present invention can be injected to a subset or subgroup of the locations described in embodiments of the present invention. The dosage at a treatment or injection site is preferably lower than a dosage that would have the effect of paralyzing a nerve or muscle and the combined dosage to multiple sites can be below, at, or higher than the treatment at a single location to have the effect of paralyzing a nerve or muscle. The dosage used in, for example, standard migraine treatment is 155 units, intramuscularly in the forehead, temporal, and cervical muscles. Side effects can include breathing difficulties, muscle weakness, problems swallowing, asthenia, muscle twitching, visual disturbances, etc. The amount of botulinum toxin to cover this area and the rest of the trigeminal, thoracic, lumbar, and sacral dermatomes that may be overproducing glutamate, Substance P, and CGRP to prevent or minimize the central sensitization effect would be unacceptably large. The large dose of botulinum toxin could produce serious side effects. The methods according to embodiments of the present invention minimize or eliminate side effects because of the much smaller amount of botulinum toxin used, and where and how it is injected to produce the neural effect without unneeded motor side effects.

In particular, the methods according to embodiments of the present invention are novel and inventive as they allow for a much smaller amount of botulinum toxin to be injected and still cover all dermatomes with no or minimal motor involvement. By using a subcutaneous or intradermal injection that reaches the unmyelinated C-fibers, it takes a lot less botulinum toxin to absorbed into the axons of unmyelinated nerves as opposed to the myelinated nerves, and there are no motor nerves in the epithelium. The injection site, for example, ½ to 1 inch from the patient's spine allows for a lower dose of botulinum toxin because there is a shorter distance to the dorsal root ganglia (approximately ¼ inch) for botulinum toxin to diffuse as compared to several feet if given in the arm or leg. The site is the only place in the body where the sensory and motor nerves are not in close proximity. This combination of low dose and separation of motor and sensory nerves by approximately 1 inch of bone and tissue between the motor and sensory nerves should minimize or eliminate any motor side effects. The cervical sensory nerves exit the spin though the dorsal root and the motor nerves exit the ventral root. Furthermore, the methods according to embodiments of the present invention do not require vagus nerve injection. The only superficial exposure of the vagus nerve is Arnold's nerve, which is in the ear canal. It is a mixed motor and sensory nerve, and the motor component of it innervates the throat. If botulinum toxin is injected into or around the Arnold's nerve, it could generate speech and swallowing problems. The inventor(s) have found that there is enough anastomosis between the sensory cervical nerves, the trigeminal nerve, and the vagus nerve that botulinum toxin can reach the vagus ganglia and stop the overproduction of Substance P, glutamate, and CGRP.

The botulinum toxin injection can be given to and/or around the vicinity of a trigeminal nerve, a cervical nerve, a thoracic nerve, a lumbar nerve, and/or a sacral nerve of the patient. Preferably, it is not necessary to inject botulinum toxin to the cranial nerves because there is numerous anastomosis between the trigeminal nerves and the spinal nerves. The trigeminal nerve to which botulinum is injected in accordance with embodiments of the present invention may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve by the subcutaneous administration minimizes or eliminates muscular side effects.

The cervical nerve to which botulinum is injected in accordance with embodiments of the present invention may include, but is not limited to, the c-2 nerve, c-3 nerve, c-4 nerve, c-5 nerve, c-6 nerve, c-7 nerve, c-8 nerve, or a combination thereof. The thoracic nerve to which botulinum is injected in accordance with embodiments of the present invention may include, but is not limited to, the t-2 to t-3 nerve, t-5 to t-6 nerve, t-7 to t-9 nerve, and/or t-10 to t-12 nerve, or a combination thereof. The lumbar nerve to which botulinum is injected in accordance with embodiments of the present invention may include, but is not limited to, the 1-1 to 1-2 nerve, 1-2 to 1-3 nerve, and/or 1-4 to 1-5 nerve, or a combination thereof. The sacral nerve to which botulinum is injected in accordance with embodiments of the present invention may include, but is not limited to, the s-1 to s-2, s-3 to s-4, and/or s-4 to s-5, or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2, 1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. In some embodiments, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for infants to children about five years of age would have to be adjusted for age and weight.

Botulinum toxin is given to lower the levels of Substance P, CGRP, and glutamate to normal. Botulinum toxin normally begins to work after about three days, when injected about ½ to an inch from the spinal cord for all spinal injections. Many original studies describe injections in the forearm or calf, and it takes about 2 weeks to begin working. In contrast, when the injection is subcutaneously given near the dorsal root ganglion to reach unmyelinated C-fibers; the toxin only takes less than two weeks to reach the height of its effectiveness. This is because it is a shorter distance to diffuse into the unprotected axons to the cell body. It is important to inject botulinum toxin near the patient's spine because there is about one inch of tissue between the motor and sensory nerves in that area and no botulinum toxin reaches the motor nerves from such an injection, which will cause side effects. In other words, the only place in the body where the motor and sensory nerves do not run in close proximity is where the nerves exit the patient's spine; sensory nerves exit the dorsal root and the motor nerves exit the ventral roots. Thus, injecting botulinum toxin near the patient's spine allows the use of botulinum toxin in all dermatomes without producing muscular side effects. For example, blood glutamate levels could be monitored to make sure that levels drop to normal and stay normal as well, and to make sure they normalize as well. Normal blood glutamate levels are known to range from 40 to 60 uM. Alternatively, one of ordinary skill in the art can have the knowledge or expertise to reasonably perceive normal blood glutamate levels. When the botulinum toxin wears off, blood tests show an increase in Substance P, glutamate, or CGRP, and/or the symptoms begin to redevelop, more botulinum toxin can be given to combat the symptoms. If the levels/symptoms fail to normalize, then if desired, a small dose of one of the glutamate antagonists can be administered to help lower glutamate levels without producing side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

In general, the therapeutically effective dosage or amount can be, for example, 1-150 units depending on the patient's body weight. The dosage for adults is, for example, about 1-150 units. For an adult, the dosage can be adjusted to their body weight and age. For toddlers (from about 1 to 5 years old), the dosage can be, for example, about 1-30 units and can be adjusted to the patient's body weight and age as well. It should be appreciated that the dosage for toddlers is estimated to be 30 units of botulinum toxin, which has been used safely since the 1990s in cerebral palsy infants and young children to control their severe muscle spasms.

In general, the total dosage can be 1-150 units depending on the patient's body weight. Preferably, the total dosage is about 50-150 units. The total dosage for adults whose weight is about 150 lbs is about 10-150 units. Preferably, the total dosage for adults whose weight is about 150 lbs is about 50-150 units. For children over about 5 years old, the total dosage can be adjusted to the child's body weight.

Botulinum toxins for use according to the present invention can be stored in lyophilized, vacuum dried form in containers under vacuum pressure or as stable liquids. Prior to lyophilization, the botulinum toxin can be combined with pharmaceutically acceptable excipients, stabilizers, and/or carriers, such as albumin. The lyophilized material can be reconstituted with saline or water to create a solution or composition containing botulinum toxin to be administered to the patient.

Preferably, the botulinum neurotoxin is peripherally administered by delivering it to or to the vicinity of the aforementioned nerve or to the aforementioned nerve branch or its ganglion nuclei. This method of administration permits the botulinum neurotoxin to be administered to and/or to affect select target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeated injections.

Diffusion of biological activity of botulinum toxin within a tissue appears to be a function of dose and can be graduated. Jankovic J., et al *Therapy with Botulium* Toxin, Marcel Dekker, Inc., (1994), page 150. Thus, diffusion of botulinum toxin can be controlled to reduce potentially undesirable side effects that may affect the patient's cognitive or motor abilities. For example, botulinum neurotoxin may be administered so that the botulinum neurotoxin primarily affects neural systems believed to be involved in selected neuropsychiatric disorders, and does not have negatively adverse effects on other neural or motor systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, a potency, dosage, or a duration may vary depending on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer, and/or carrier. If lyophilized, the botulinum toxin may be reconstituted with saline or water to make a solution or composition to be administered to the patient. Alternatively, a composition administered to a patient comprises botulinum toxin(s) and other pharmaceutically active ingredients.

Illustrative embodiments are explained in the following example of a case study conducted with a patient having arrhythmia.

Example 1

Patient is a 34-year-old female. The patient weighs about 170 lbs. She has suffered from cardiac arrhythmia, severe migraines, TMJ, anxiety/depression, sleep problems (sleeps 3-4 hours and wakes up and can't go back to sleep), occasional vertigo, neck and shoulder blade cramps and pain, overactive bladder, chronic cold sensitivity, pain down the back of the leg, pain and sensitivity in the bottom of her feet, knee pain, reading and comprehension problems, and chronic fatigue. Patient has been to a cardiologist and was prescribed beta blockers for her severe cardiac arrhythmias which did not work and made her feel bad, so she quit taking them. She had a back operation 2½ months ago, which did not help her lower back pain. She received botulinum toxin in the trigeminal, cervical, thoracic chamber, and sacral regions (subcutaneous or intradermal injection, 2 units of botulinum toxin to and/or around the vicinity of an ophthalmic, maxillary, and/or mandibular nerve of the trigeminal nerve bilaterally, lateral to the patient's spine, 2 units to and/or around the vicinity of the c-2 to c-3, c-4 to c-6, and/or c-7 to c-8 of the cervical nerve bilaterally, lateral to the patient's spine, 2 units to and/or around the vicinity of the t-2 to t-3, t-5 to t-6, t-7 to t-9, and/or t-10 to t-12 of the thoracic nerve bilaterally, lateral to the patient's spine, 2 unit to and/or around the vicinity of the 1-1 to 1-2, 1-2 to 1-3, and/or 1-4 to 1-5 of the lumbar nerve bilaterally, lateral to the patient's spine, and/or 2 units to and/or around the vicinity of the s-1 to s-2, s-3 to s-4, and/or s-4 to s-5 of the sacral nerve bilaterally, lateral to the patient's spine, total of 52 units) on Nov. 8, 2019. After two weeks, on Nov. 22, 2019, she said that basically all the previously mentioned symptoms were gone, including her cardiac arrhythmias, which was confirmed by arrhythmia monitoring. The conversation is recorded as follows. "Friday afternoon, I got the shots and went home and felt sore that night. The weekend through Monday, I did not notice any changes other than feeling sore from the injections. Tuesday morning, I felt really good, I woke up without a headache, my jaw was not hurting, and I did not notice any palpitations. Wednesday and Thursday, I had several palpitations, but they did not feel like they normally felt, not any worse but I could tell something was going on. Friday, it slowly started to ease up. I was feeling so much better and went to my follow up appointment with my back surgeon; all my back pain was gone. He told me I looked great and was doing so good. Seven days after the injections, on Saturday and Sunday, I had a few palpitations, but they were faint. Monday, I had some but not very much chest pressure, but I can tell that my body is trying to stop them when the premature ventricular contractions (PVC) try to happen. I am starting a new job in a whole new setting, so I am a little nervous and maybe that is why I feel them. Tuesday and Wednesday, I felt about the same, and Thursday, I had my first day at my new job and I only noticed a few palpitations, but they felt more like a muscle spasm or a hiccup. Today is Friday which is 14 days since my injections. My headaches are gone, my temporomandibular joints (TMJ) are not bothering me, my stomach cramping is almost nonexistent, and my heart issues (PVCs and palpitations) are a lot better. The things that I feel are more like a muscle spasm or hiccups than what I was feeling before, the back pain that I was having is gone, and I get a little sore but that's only when I overwork or sit too long but it's not like it was before the injections. The last two days I have hardly even noticed anything different about my heart, it's just been normal days."

The following is the patient's detailed medical history.
Current Medications:
  Calcium and vitamin D three times a day.
  Tylenol and Ibuprofen as needed.

Past Surgeries:
  Emergency surgery to repair right ovary after it burst in 2000
  Tonsillectomy with adenoids removed
  Gallbladder removed
  Two C-sections
  Impacted wisdom teeth removed
  Ligament repair on left ankle
  Breast reduction
  Tummy tuck
  Partial hysterectomy
  Spinal fusion from L4-S1
Effects of Botulinum Toxin Injections:
  The patient's lower back spasms and muscle cramps in neck and shoulder blades are gone.
  The patient's migraines are gone.
  The patient's issues with overactive bladder are gone.
  The patient's TMJ is so much better; jaw doesn't "lock" like it used to.
  The patient no longer wakes up stiff.
  The patient's dry eyes have improved.
  The patient's chronic pain and general pain are so much better. The only time it doesn't feel good is when she is overworked since her back is still healing. (Plus, she has been slacking with her exercises while she is getting her new schedule down).
  With the chronic fatigue, the patient experiences feeling worn out in the evening but is still adjusting to a new job, stays busy 8 hours a day (before botulinum toxin injections, she used to lie down a few times a week), and feels great on the weekends just adjusting to a new schedule.
  The patient's depression has improved. She no longer cries; She feels mentally better.
  The patient no longer feels foggy all the time.
  The patient's anxiety has improved, which was expected to worsen because she was more nervous, starting a job in an office setting in which she has never worked before. The patient was a little nervous but not making herself sick with anxiety like she would have before.
  The patient no longer has cramps with IBS like before.
  The patient doesn't wake up at all hours of the night like before.
  The patient experiences a tiny bit of acid reflux but it feels better than before.
  The patient feels that her arrhythmias are gone. She wears a smart watch that buzzes when her heart rate gets too high. It used to buzz all the time when her arrhythmias were out of control. Now it does not. She is under constant monitoring even if she is not equipped with medical equipment.
Three months after the botulinum toxin injections on Nov. 8, 2019:
  The patient felt a few rapid heart rates occasionally. The next day, she received a total of 16 units of botulinum toxin (4 units in the t-1 to t-3 dermatome bilaterally and 4 units in the t-6 to t-8 dermatome bilaterally). 4 days later, arrhythmias were gone again and after about a month, all arrhythmia symptoms were still gone.
  The claimed invention proposes to treat some if not all of the 30% of cardiac arrhythmias not caused by direct problems to the heart. It will be necessary to give the botulinum toxin not only to the directly involved dermatomes (t-1 to t-3, t-6 to t-8, and vagus nerve) but also the rest of the sensory dermatomes because if these areas are overproducing the excitatory neural peptides, they can diffuse up and down the spinal cord and produce overstimulation of other nerves by a process called central stimulation. Current botulinum toxin injection methods would require large amounts and could possibly cause dangerous side effects. The claimed invention proposes a novel way to lower the botulinum toxin dosage to stop side effects while still preventing the neuropathic problems.

1. Subcutaneous or intradermal injections of the botulinum toxin just under the skin. In this area are found unmyelinated C fibers. It takes far less botulinum toxin to penetrate the unmyelinated fibers than axons that are protected by myelin
2. Injection approximately ½-1 inch from the patient's spine this allows for an even lower dose as it is a shorter distance to the cell bodies for the botulinum toxin to diffuse where the glutamate, Substance P, and CGRP are being overproduced
3. This injection site is also where the motor and sensory nerves exit the patient's spine. The sensory nerves exit from the dorsal root and the motor nerves exit from the ventral root. This is the only place in the body where the sensory and motor nerves are separated (by about %-1 inch of tissue) so there will be little if any botulinum toxin effects on the motor nerves.

The claimed invention has shown that there is numerous anastomosis between the spinal, trigeminal and the cranial nerves which includes the vagus nerve, which slows the heart rate. The vagus is a mixed motor and sensory nerve and all its nerves are myelinated so it would take larger dosages to be injected into one of its branches like Arnold's nerve which is inside the ear canal, to reach the vagus nerve, but this could possibly cause significant motor effects.

Unless defined otherwise, all technical and scientific terms used herein have the same meaning as commonly understood by the person of ordinary skill in the art to which this invention belongs. Thus the scope of the embodiments of the present invention should be determined by the appended claims and their legal equivalents.

It should be understood that the above description of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating arrhythmia in a patient in need thereof,
comprising administering botulinum toxin to the patient, thereby treating arrhythmia, wherein the administering for an adult comprises, by subcutaneous or intradermal injection, injecting 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine.

2. The method of claim 1, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein the cervical nerve comprises a c-2 nerve, c-3 nerve, c-4 nerve, c-5 nerve, c-6 nerve, c-7 nerve, c-8 nerve, or a combination thereof.

4. The method of claim 1, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

5. The method of claim 1, wherein the lumbar nerve comprises an l-1 nerve, l-2 nerve, l-3 nerve, l-4 nerve, l-5 nerve, or a combination thereof.

6. The method of claim 1, wherein the sacral nerve comprises an s-1 nerve, s-2 nerve, s-3 nerve, s-4 nerve, s-5 nerve, or a combination thereof.

7. The method of claim 1, wherein the botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

8. The method of claim 1, wherein each of the subcutaneous or intradermal injection is bilateral.

9. The method of claim 1, wherein a total dosage of the botulinum toxin for an adult who weighs about 150 lbs is between about 2 and about 150 units.

10. The method of claim 1, wherein a total dosage of the botulinum toxin for an adult, a child over about 5 years old, and a toddler from about 1 to 5 years old is adjusted for age, weight, or a combination thereof.

11. A method for treating arrhythmia in a patient in need thereof, comprising administering botulinum toxin to the patient, thereby treating arrhythmia, wherein the administering for an adult comprises, by subcutaneous or intradermal injection, injecting 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine,
wherein a maximum total dosage of the botulinum toxin is 150 units.

12. The method of claim 11, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

13. The method of claim 11, wherein the cervical nerve comprises a c-2 nerve, c-3 nerve, c-4 nerve, c-5 nerve, c-6 nerve, c-7 nerve, c-8 nerve, or a combination thereof.

14. The method of claim 11, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

15. The method of claim 11, wherein the lumbar nerve comprises an l-1 nerve, l-2 nerve, l-3 nerve, l-4 nerve, l-5 nerve, or a combination thereof.

16. The method of claim 11, wherein the sacral nerve comprises an s-1 nerve, s-2 nerve, s-3 nerve, s-4 nerve, s-5 nerve, or a combination thereof.

17. The method of claim 11, wherein the administered botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

18. The method of claim 11, wherein each of the subcutaneous or intradermal injection is bilateral.

\* \* \* \* \*